(12) United States Patent
Overby et al.

(10) Patent No.: US 7,250,550 B2
(45) Date of Patent: Jul. 31, 2007

(54) SYNTHETIC BONE SUBSTITUTE MATERIAL

(75) Inventors: Robyn J. Overby, Memphis, TN (US);
Olaf H. Schulz, Arlington, TN (US);
Ann V. Burgess, Cordova, TN (US);
Warren O. Haggard, Bartlett, TN (US); Michael Vincent, Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 10/972,255

(22) Filed: Oct. 22, 2004

(65) Prior Publication Data
US 2006/0088601 A1 Apr. 27, 2006

(51) Int. Cl.
*A61F 2/28* (2006.01)
(52) U.S. Cl. ....................................................... 623/16
(58) Field of Classification Search ................. 623/16, 623/11, 18; 424/549
See application file for complete search history.

(56) References Cited

U.S. PATENT DOCUMENTS

| | | | |
|---|---|---|---|
| 3,090,094 A | 5/1963 | Schwartzwalder et al. |
| 3,616,841 A | 11/1971 | Walz |
| 3,662,405 A | 5/1972 | Bortz et al. |
| 3,790,365 A | 2/1974 | Niebylski et al. |
| 3,813,312 A | 5/1974 | Kinkade et al. |
| 3,816,952 A | 6/1974 | Niebyski et al. |
| 3,829,326 A | 8/1974 | Soejima et al. |
| 3,899,556 A | 8/1975 | Heide et al. |
| 3,905,047 A | 9/1975 | Long |
| 4,000,525 A | 1/1977 | Klawitter et al. |
| 4,076,888 A | 2/1978 | Perugini et al. |
| 4,158,684 A | 6/1979 | Klawitter et al. |
| 4,168,326 A | 9/1979 | Broemer et al. |
| 4,222,128 A | 9/1980 | Tomonaga et al. |
| 4,237,559 A | 12/1980 | Borom |
| 4,365,356 A | 12/1982 | Broemer et al. |
| 4,371,484 A | 2/1983 | Inukai et al. |
| 4,430,760 A | 2/1984 | Smestad |
| 4,447,548 A | 5/1984 | Huebsch, III |
| 4,517,069 A | 5/1985 | Harney et al. |
| 4,568,536 A | 2/1986 | Kronenthal et al. |
| 4,595,713 A | 6/1986 | St. John |
| 4,599,085 A | 7/1986 | Riess et al. |
| 4,612,009 A | 9/1986 | Drobnik et al. |
| 4,619,655 A | 10/1986 | Hanker et al. |
| 4,626,392 A | 12/1986 | Kondo et al. |
| 4,629,464 A | 12/1986 | Takata et al. |
| 4,650,665 A | 3/1987 | Kronenthal et al. |
| 4,654,314 A | 3/1987 | Takagi et al. |
| 4,681,763 A | 7/1987 | Nathanson et al. |
| 4,693,986 A | 9/1987 | Vit et al. |
| 4,777,153 A | 10/1988 | Sonuparlak et al. |
| 4,794,046 A | 12/1988 | Nagai |
| 4,810,685 A | 3/1989 | Twigg et al. |
| 4,820,306 A | 4/1989 | Gorman et al. |
| 4,880,660 A | 11/1989 | Aasen et al. |
| 4,882,149 A | 11/1989 | Spector |
| 4,892,734 A | 1/1990 | Leonard |
| 4,950,294 A | 8/1990 | Hakamatsuka |
| 4,957,509 A | 9/1990 | Tamari et al. |
| 4,960,426 A | 10/1990 | Atsumi |
| 4,967,509 A | 11/1990 | Storey et al. |
| 4,969,913 A | 11/1990 | Ojima |
| 4,975,526 A | 12/1990 | Kuberasampath et al. |
| 4,994,030 A | 2/1991 | Glowczewskie et al. |
| 5,015,610 A | 5/1991 | Dwivedi |
| 5,030,396 A | 7/1991 | Saita et al. |
| 5,061,286 A | 10/1991 | Lyle |
| 5,061,660 A | 10/1991 | Park et al. |
| 5,073,373 A | 12/1991 | O'Leary et al. |
| 5,141,510 A | 8/1992 | Takagi et al. |
| 5,147,403 A | 9/1992 | Gitelis |
| 5,152,791 A | 10/1992 | Hakamatsuka et al. |
| 5,158,726 A | 10/1992 | Saita et al. |
| 5,162,114 A | 11/1992 | Kuberasampath et al. |
| 5,171,720 A | 12/1992 | Kawakami |
| 5,192,325 A | 3/1993 | Kijima et al. |

(Continued)

FOREIGN PATENT DOCUMENTS

EP 0 263 489 A1 4/1988

(Continued)

OTHER PUBLICATIONS

Wright Medical Group Inc., Cellplex TCP granules- a synthetic cancellous bone substitite. see at http://www.wrightmedicalgroup.com. pp. 1-7, p. 7, in particular, Jul. 24, 2003.*

(Continued)

*Primary Examiner*—Sandra E. Saucer
*Assistant Examiner*—Satyendra K. Singh
(74) *Attorney, Agent, or Firm*—Alston & Bird LLP

(57) ABSTRACT

The invention includes a synthetic bone substitute material suitable for use as a replacement for cancellous bone in a bone graft composition, the material comprising a reticulated framework of interconnecting bioceramic struts defining an interconnecting interstitial void volume, and a solid non-porous composition substantially filling the interstitial void volume and in intimate contact with the reticulated framework, the pore-filling composition comprising calcium sulfate. Calcium triphosphate is a preferred bioceramic material for the reticulated framework.

23 Claims, 1 Drawing Sheet

U.S. PATENT DOCUMENTS

| | | | |
|---|---|---|---|
| 5,211,664 A | 5/1993 | Tepic et al. |
| 5,219,897 A | 6/1993 | Murray |
| 5,236,456 A | 8/1993 | O'Leary et al. |
| 5,236,971 A | 8/1993 | Murray |
| 5,264,214 A | 11/1993 | Rhee et al. |
| 5,281,251 A | 1/1994 | Kenny et al. |
| 5,282,861 A | 2/1994 | Kaplan |
| 5,284,655 A | 2/1994 | Bogdansky et al. |
| 5,284,695 A | 2/1994 | Barlow et al. |
| 5,290,558 A | 3/1994 | O'Leary et al. |
| 5,296,180 A | 3/1994 | Hayes et al. |
| 5,298,254 A | 3/1994 | Prewett et al. |
| 5,306,304 A | 4/1994 | Gendler |
| 5,306,673 A | 4/1994 | Hermansson et al. |
| 5,314,476 A | 5/1994 | Prewett et al. |
| 5,314,478 A | 5/1994 | Oka et al. |
| 5,320,844 A | 6/1994 | Liu |
| 5,336,699 A | 8/1994 | Cooke et al. |
| 5,356,629 A | 10/1994 | Sander et al. |
| 5,366,507 A | 11/1994 | Sottosanti |
| 5,385,887 A | 1/1995 | Yim et al. |
| 5,397,362 A | 3/1995 | Noda |
| 5,397,759 A | 3/1995 | Torobin |
| 5,405,390 A | 4/1995 | O'Leary et al. |
| 5,417,975 A | 5/1995 | Lussi et al. |
| 5,425,769 A | 6/1995 | Snyders, Jr. |
| 5,439,684 A | 8/1995 | Prewett et al. |
| 5,462,722 A | 10/1995 | Liu et al. |
| 5,482,551 A | 1/1996 | Morris et al. |
| 5,484,601 A | 1/1996 | O'Leary et al. |
| 5,507,813 A | 4/1996 | Dowd et al. |
| 5,510,396 A | 4/1996 | Prewett et al. |
| 5,512,610 A | 4/1996 | Lin |
| 5,531,791 A | 7/1996 | Wolfinbarger, Jr. |
| 5,531,794 A | 7/1996 | Takagi et al. |
| 5,569,308 A | 10/1996 | Sottosanti |
| 5,573,771 A | 11/1996 | Geistlich et al. |
| 5,578,662 A | 11/1996 | Bennett et al. |
| 5,614,206 A | 3/1997 | Randolph et al. |
| 5,618,549 A | 4/1997 | Patat et al. |
| 5,624,674 A | 4/1997 | Seare, Jr. |
| 5,639,402 A | 6/1997 | Barlow et al. |
| 5,676,146 A | 10/1997 | Scarborough |
| 5,676,699 A | 10/1997 | Gogolewski et al. |
| 5,681,572 A | 10/1997 | Seare, Jr. |
| 5,681,873 A | 10/1997 | Norton et al. |
| 5,697,981 A | 12/1997 | Ison et al. |
| 5,700,289 A | 12/1997 | Breitbart et al. |
| 5,702,449 A | 12/1997 | McKay |
| 5,707,962 A | 1/1998 | Chen et al. |
| 5,714,103 A | 2/1998 | Bauer et al. |
| 5,727,945 A | 3/1998 | Dannenbaum |
| 5,756,127 A | 5/1998 | Grisoni et al. |
| 5,763,416 A | 6/1998 | Bonadio et al. |
| 5,766,618 A | 6/1998 | Laurencin et al. |
| 5,769,897 A | 6/1998 | Härle |
| 5,788,976 A | 8/1998 | Bradford |
| 5,807,567 A | 9/1998 | Randolph et al. |
| 5,824,087 A | 10/1998 | Aspden et al. |
| 5,830,493 A | 11/1998 | Yokota et al. |
| 5,861,445 A | 1/1999 | Xu et al. |
| 5,899,939 A | 5/1999 | Boyce et al. |
| 5,910,315 A | 6/1999 | Stevenson et al. |
| 5,925,444 A | 7/1999 | Katsumura et al. |
| 5,948,426 A | 9/1999 | Jefferies |
| 5,948,428 A | 9/1999 | Lee et al. |
| 5,954,867 A * | 9/1999 | Chow et al. ............ 106/35 |
| 5,964,805 A | 10/1999 | Stone |
| 5,972,368 A | 10/1999 | McKay |
| 5,981,828 A | 11/1999 | Nelson et al. |
| 6,022,509 A | 2/2000 | Matthews et al. |
| 6,030,635 A | 2/2000 | Gertzman et al. |
| 6,030,636 A | 2/2000 | Randolph et al. |
| 6,037,519 A | 3/2000 | McKay |
| 6,051,247 A | 4/2000 | Hench et al. |
| 6,056,970 A | 5/2000 | Greenawalt et al. |
| 6,071,530 A | 6/2000 | Polson et al. |
| 6,083,522 A | 7/2000 | Chu et al. |
| 6,118,043 A | 9/2000 | Nies et al. |
| 6,136,029 A | 10/2000 | Johnson et al. |
| 6,149,688 A | 11/2000 | Brosnahan et al. |
| 6,224,635 B1 | 5/2001 | Ricci et al. |
| 6,296,667 B1 | 10/2001 | Johnson et al. |
| 6,334,856 B1 | 1/2002 | Allen et al. |
| 6,340,477 B1 | 1/2002 | Anderson |
| 6,527,810 B2 | 3/2003 | Johnson et al. |
| 6,652,887 B1 | 11/2003 | Richelsoph et al. |
| 6,863,899 B2 | 3/2005 | Koblish et al. |
| 2001/0018614 A1 | 8/2001 | Bianchi |
| 2002/0016636 A1 | 2/2002 | Ricci et al. |
| 2002/0169066 A1 | 11/2002 | Cassidy et al. |
| 2002/0197315 A1 | 12/2002 | Haggard et al. |
| 2004/0024081 A1 | 2/2004 | Trieu et al. |

FOREIGN PATENT DOCUMENTS

| | | |
|---|---|---|
| EP | 0 335 359 A2 | 10/1989 |
| WO | WO 89/07917 A1 | 9/1989 |
| WO | WO 91/00252 A1 | 1/1991 |
| WO | WO 91/17722 A1 | 11/1991 |
| WO | WO 96/39203 A1 | 12/1996 |
| WO | WO 98/22041 A1 | 5/1998 |
| WO | WO 98/40113 A1 | 9/1998 |
| WO | WO 99/15150 A1 | 4/1999 |
| WO | WO 99/16478 A1 | 4/1999 |
| WO | WO 99/16479 A1 | 4/1999 |
| WO | WO 00/74690 A1 | 12/2000 |
| WO | WO 01/12106 A1 | 2/2001 |
| WO | WO 02/05750 A2 | 1/2002 |
| WO | WO 02/05861 A1 | 1/2002 |
| WO | WO 02/068009 A2 | 9/2002 |
| WO | WO 03/024316 A2 | 3/2003 |
| WO | WO 03/030956 A2 | 4/2003 |
| WO | WO 03/053488 A1 | 7/2003 |

OTHER PUBLICATIONS

Adkisson et al., "Rapid Quantitative Bioassay of Osteoinduction", *J. Orthop. Res.*, 2000, p. 503-511, vol. 18.

Betz, Randal R., "Limitations of Autograft and Allograft: New Synthetic Solutions", *Orthopedics*, 2002, pp. s561-s570, vol. 25, Supplement 5.

Greenwald et al., "Bone-Graft Substitutes: Facts, Fictions, and Applications", *J. Bone Joint Surg.*, 2001, pp. 98-103, vol. 83-A, Supplement 2, Part 2.

Hanker et al., "Scanning Electron Microscopy of Composite Hydroxylapatite/Plaster Implants for Bone Reconstruction", *Proc. 44th Mtg. Electron Microscopy Soc. of America*, 1986, pp. 326-327.

Kelly, Evelyn B., "New Frontiers in Bone Grafting", *Orthopedic Technology Review*, 2000, vol. 2, No. 9.

Turner et al., "Radiographic and Histologic Assessment of Calcium Sulfate in Experimental Animal Models and Clinical Use as a Resorbable Bone-Graft Substitute, a Bone-Graft Expander, and a Method for Local Antibiotic Delivery", *J. Bone Joint Surg.*, 2001, pp. 8-18. vol. 83-A, Supplement 2, Part. 1.

"Advances in Biomaterials for Bone Regeneration", *Orthopedics*, May 2003, pp. s545-s596, vol. 26, No. 5 Supplement.

"Bone Graft Substitutes Safe, Effective", AMA Science New Media Briefings, Dec. 6, 2001.

"Biomaterials Tutorial", www.btec.cmu.edu/tutorial/biomaterials/biomaterials.htm, undated.

Charrière et al., "Mechanical Characterization of Brushite and Hydroxyapatite Cements", *Biomaterials*, 2001, pp. 2937-2945, vol. 22.

Nadkami et al., "An In Vivo Evaluation of Calcium Sulfate Composite Graft Materials Using Rabbit Metaphyseal and Calvarial Defects", Poster Sesion—Bone Grafts—Valencia D, 46th Annual Meeting, Orthopaedic Research Society, Mar. 12-15, 2000, Orlando, Florida, p. 0683.

Cleere, et al. "In-vitro Dissolution Characteristics of Calcium Phosphate/Calcium Sulphate Based Hybrid Biomaterials," *Key Engineering Materials*, 2004, pp. 585-588, vols. 254-256.

Grimandi et al. "In vitro Evaluation of a New Injectable Calcium Phosphate Material," *J. Biomed Mater Res*, 1998, pp. 660-666, vol. 39.

Hanker et al. "Setting of Composite Hydroxyapatite/Plaster Implants with Blood for Bone Reconstruction," *Proceedings of the 44th Annual Meeting of the Electron Microscopy Society of America*, 1986, pp. 328-329.

Nilsson, et al. "Factors Influencing the Compressive Strength of an Injectable Calcium Sulfate- Hydroxyapatite Cement," *Journal of Material Science: Materials in Medicine*, 2003, pp. 399-404, vol. 14.

Sato et al. "Osteogenic Response of Rabbit Tibia to Hydroxyapatite Particle-Plaster of Paris Mixture," *Biomaterials*, 1998, pp. 1895-1900, vol. 19.

* cited by examiner

SYNTHETIC BONE SUBSTITUTE MATERIAL

FIELD OF THE INVENTION

The invention is directed to a synthetic bone substitute material suitable for use as a replacement for cancellous bone in a bone graft composition, bone graft compositions comprising the synthetic bone substitute material, and methods of making and using the synthetic bone substitute material.

BACKGROUND OF THE INVENTION

Defects in bone structure arise in a variety of circumstances, such as trauma, disease, and surgery. There is a need for effective repair of bone defects in various surgical fields, including maxillo-craniofacial, periodontics, and orthopedics. Numerous natural and synthetic materials and compositions have been used to stimulate healing at the site of a bone defect. As with compositions used to repair other types of tissue, the biological and mechanical properties of a bone repair material are critical in determining the effectiveness and suitability of the material in any particular application.

After blood, bone is the second most commonly transplanted material. Autologous cancellous bone has long been considered the most effective bone repair material, since it is both osteoinductive and non-immunogenic. However, the use of autologous cancellous bone is not available under all circumstances, and donor site morbidity and trauma are serious drawbacks to this approach. The use of allograft bone avoids the problem of creating a second surgical site in the patient, but suffers from some disadvantages of its own. For instance, allograft bone typically has a lower osteogenic capacity than autograft bone, a higher resorption rate, creates less revascularization at the site of the bone defect, and typically results in a greater immunogenic response. The transfer of certain diseases is also a danger when using allografts.

To avoid the problems associated with autograft and allograft bone, considerable research has been conducted in the area of synthetic bone substitute materials that can be used in lieu of natural bone material. For example, various compositions and materials comprising demineralized bone matrix, calcium phosphate, and calcium sulfate have been proposed. In many instances, however, the synthetic bone materials proposed in the art have suffered from significant disadvantages. For example, some compositions fail to provide the structural support necessary to augment the healing process. Other compositions fail to adequately mimic the density and overall physical structure of natural bone, which can lead to reduced performance. This can be particularly problematic when replacing cancellous (trabecular) bone material, which has a distinct reticulated pore structure that can be difficult to mimic in a synthetic construct. Further, some materials suffer from a reabsorption rate that improperly paces the natural healing process and, thus, fail to provide the necessary framework for the ingrowth of new tissue.

There remains a need in the art for improved bone substitute materials suitable for use in bone graft compositions, particularly materials that can be used as a replacement for cancellous bone.

BRIEF SUMMARY OF THE INVENTION

The present invention provides a synthetic bone substitute material suitable for use as a replacement for cancellous bone in a bone graft composition. The bone substitute material of the invention comprises a reticulated bioceramic framework that exhibits a pore structure that closely resembles natural cancellous bone, thus providing a hospitable environment for cellular infiltration during healing. The interconnected structure created by the reticulated framework provides scaffolding where mesenchymal stem cells can multiply and differentiate into bone forming cells. The bone substitute material of the invention also includes a solid non-porous composition substantially filling the interstitial void volume within the reticulated framework. The void-filling composition comprises calcium sulfate. The use of calcium sulfate to plug the pores of the reticulated framework advantageously results in a material exhibiting two different resorption rates. The calcium sulfate pore-filling material will be resorbed more quickly in the early stages of the healing process, leaving the reticulated framework for ingrowth of new tissue. The presence of the calcium sulfate also strengthens the construct, which improves stability of the reticulated structure following implantation, as well as stability of the material during manufacture and handling.

Thus, in one aspect, the invention provides a synthetic bone substitute material suitable for use as a replacement for cancellous bone in a bone graft composition, wherein the material includes a reticulated framework comprising a plurality of interconnecting bioceramic struts and defining an interconnecting interstitial void volume, and a solid, non-porous composition substantially filling the interstitial void volume and in intimate contact with the reticulated framework, the pore-filling composition comprising calcium sulfate. Preferably, the outer surface of the reticulated framework is also coated with the pore-filling calcium sulfate composition. The bone substitute material may take a variety of forms, including pellets, granules, wedges, blocks and disks of various sizes.

In another embodiment, the synthetic bone substitute material comprises a plurality of granules dispersed as a discontinuous phase within a solid matrix composition comprising calcium sulfate. The granules comprise the reticulated bioceramic framework filled with a calcium sulfate composition as described above. In this embodiment, the material can be carved into blocks or other desired shapes as dictated by surgical requirements, such as the size and shape of the bone defect, or the material can be granulated to relatively uniform granular sizes.

The bioceramic struts can be formed from any biocompatible bioceramic material, such as alumina, zirconia, calcium phosphate, silica-based glass, pyrolytic carbon, and combinations or mixtures thereof. In one preferred embodiment, the bioceramic struts are formed of sintered calcium phosphate. The calcium phosphate used in the bioceramic struts may vary. Exemplary calcium phosphate materials include hydroxyapatite, tricalcium phosphate, tetracalcium phosphate, anhydrous dicalcium phosphate, monocalcium phosphate monohydrate, dicalcium phosphate dihydrate, heptacalcium phosphate, octocalcium phosphate, calcium pyrophosphate, oxyapatite, calcium metaphosphate, carbonatoapatite, dahlite, and combinations or mixtures thereof. In a preferred embodiment, the calcium phosphate is α-tricalcium phosphate, β-tricalcium phosphate, or a mixture thereof.

The solid non-porous calcium sulfate composition may include further ingredients, such as demineralized bone matrix, accelerants designed to accelerate the reaction of calcium sulfate hemihydrate to calcium sulfate dihydrate, plasticizers, or biologically active agents.

In another aspect, the invention provides a synthetic malleable bone graft substitute composition comprising the synthetic bone substitute material described above. The malleable bone graft substitute composition has the consistency of a putty or paste, and can be shaped into any desired form depending on the particular surgical application. For instance, the malleable bone graft substitute material of the invention can be shaped to match the particular dimensions of a specific bone defect at the time of surgery. The synthetic malleable bone graft substitute material comprises an aqueous mixing solution, calcium sulfate, a plasticizer, demineralized bone matrix, and a plurality of granules comprising a reticulated framework of interconnecting bioceramic struts that define an interconnecting interstitial void volume and a solid, non-porous calcium sulfate composition substantially filling the interstitial void volume and in intimate contact with the reticulated bioceramic framework.

The aqueous mixing solution preferably comprises sterile water and, optionally, one or more additives such as inorganic salts and surface active agents. The calcium sulfate material is preferably selected from the group selected of α-calcium sulfate hemihydrate, β-calcium sulfate hemihydrate, calcium sulfate dihydrate and mixtures thereof. Exemplary plasticizers include glycerol and other polyols, vinyl alcohol, stearic acid, hyaluronic acid, cellulose derivatives and mixtures thereof.

In a further aspect of the invention, a method for forming a synthetic bone substitute material is provided. The method involves providing a reticulated bioceramic framework comprising a plurality of interconnecting bioceramic struts and defining an interconnecting interstitial void volume and applying an aqueous calcium sulfate composition to the reticulated framework such that the aqueous calcium sulfate composition substantially fills the interstitial void volume of the reticulated framework. The method of applying the calcium sulfate composition may include, for example, injecting the composition into the reticulated framework or immersing the reticulated framework within an aqueous calcium sulfate composition. In one embodiment, granules of the reticulated framework are immersed in an aqueous calcium sulfate composition. The granules can remain in the aqueous calcium sulfate composition until the calcium sulfate sets and hardens into a solid form, or the granules can be removed after giving the calcium sulfate solution sufficient time to substantially fill the interstitial void volume of the granules. The calcium sulfate within the separated granules can then be allowed to set and harden into a solid form.

In yet another aspect of the invention, a method for treating a bone defect is provided, wherein the synthetic bone substitute material of the invention is applied to the site of a bone defect in a patient. The synthetic bone substitute material may be applied to the site of the bone defect in any of the variety of forms discussed above. For example, the synthetic bone substitute material can be applied to the surgical site in the form of pellets, granules, wedges, blocks and disks. The synthetic bone substitute material can also be applied in the form of a shaped bone graft substitute material putty or paste formed using the synthetic malleable bone graft substitute composition described above.

BRIEF DESCRIPTION OF THE DRAWING

Figure 1:
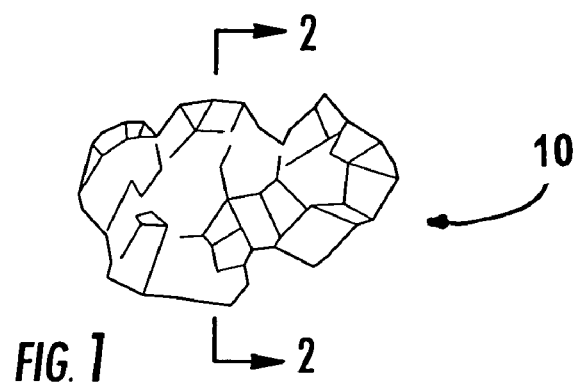
Figure 2:
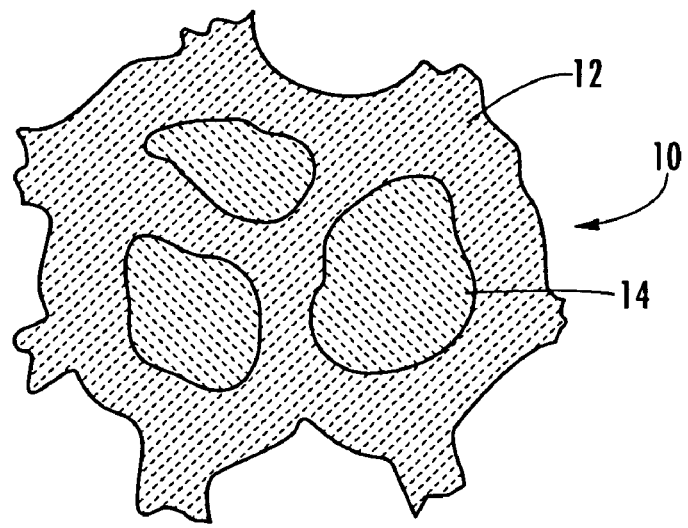

Having thus described the invention in general terms, reference will now be made to the accompanying drawings, which are not necessarily drawn to scale, and wherein:

FIG. 1 is a granule of synthetic bone substitute material according to one embodiment of the invention;

FIG. 2 is a cross-sectional view of the granule of FIG. 1; and

Figure 3:
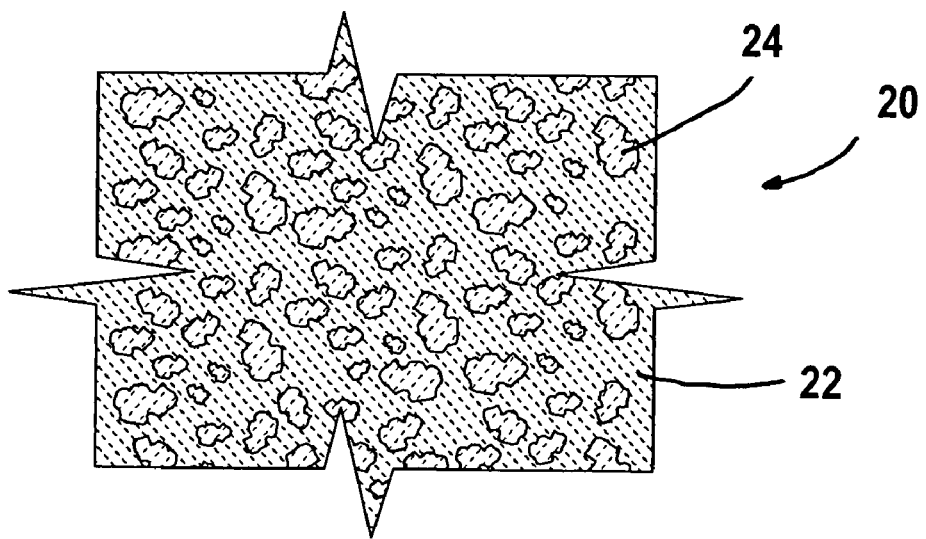

FIG. 3 is a cross-sectional view of a synthetic bone substitute material comprising a calcium sulfate matrix and a plurality of granules within the matrix.

DETAILED DESCRIPTION OF THE INVENTION

The present inventions now will be described more fully hereinafter with reference to the accompanying drawing, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The invention provides a synthetic bone substitute material that closely resembles natural cancellous bone in structure and, thus, is suitable for use as a replacement for natural cancellous bone in a bone graft composition. In one preferred embodiment, the synthetic bone substitute material is used in the form of granules of a defined structure. An exemplary granule 10 is shown in FIG. 1. A cross-sectional view of the granule of bone substitute material 10 is shown in FIG. 2. As shown, the granule 10 comprises a reticulated bioceramic framework 12 that comprises a plurality of interconnecting bioceramic struts that define an interconnecting interstitial void volume. The interstitial void volume is filled with a calcium sulfate composition 14. In a preferred embodiment, the calcium sulfate composition 14 is a solid non-porous composition that substantially fills the interstitial void volume of the reticulated framework 12 and is in intimate contact with the reticulated framework, meaning there are no intermediate layers between the calcium sulfate composition and the surface of the bioceramic struts of the framework. Instead, the calcium sulfate composition is adjacent to, and coated on, the surface of the bioceramic struts.

As will be understood, the term "bioceramic" refers to biocompatible ceramic materials that are non-toxic and suitable for implantation into the body, such as the body of a human patient or other mammal. The bioceramics used in the present invention are also typically bioactive, meaning the material solicits a specific biological response at the interface between the material and surrounding tissue of the host. However, the bioceramic material can be nearly inert, meaning there is minimal interaction with host tissues and the implant is covered with a non-adherent fibrous tissue after implantation. Further, the bioceramic material can be resorbable, meaning all or a portion of the implant chemically dissolves or is removed from the body by the host. In this case, there is no fixation, only replacement of the implant with biological tissues. Exemplary ceramic materials include alumina, zirconia, calcium phosphate, silica-based glass, pyrolytic carbon, and combinations or mixtures thereof.

The term "combinations" in this context is meant to encompass embodiments wherein more that one type of ceramic material is used in the same bone substitute material.

For example, the plurality of interconnecting bioceramic struts can include struts made of one ceramic material and struts made of a second ceramic material. In addition, the invention includes "mixtures" of ceramic materials, wherein each strut of the interconnecting network of struts is formed from a homogeneous mixture of two or more ceramic materials.

In a preferred form, the bioceramic struts are constructed of sintered calcium phosphate. A sintered calcium phosphate reticulated network is commercially available under the trade name CELLPLEX® (Wright Medical Technology, Inc., Arlington, Tenn.). The calcium phosphate used in the bioceramic struts may vary. Exemplary calcium phosphate materials include hydroxyapatite, tricalcium phosphate (e.g., α-tricalcium phosphate, β-tricalcium phosphate), tetracalcium phosphate, anhydrous dicalcium phosphate, monocalcium phosphate monohydrate, dicalcium phosphate dihydrate, heptacalcium phosphate, octocalcium phosphate, calcium pyrophosphate, oxyapatite, calcium metaphosphate, carbonatoapatite, dahlite, and combinations or mixtures thereof. In a preferred embodiment, the calcium phosphate is α-tricalcium phosphate, β-tricalcium phosphate, or a mixture thereof. In one particularly preferred embodiment, the bioceramic strut is a mixture comprising a crystalline content of about 17 to about 42 percent α-tricalcium phosphate and about 58 to about 83 percent β-tricalcium phosphate.

A calcium phosphate or other bioceramic reticulated framework useful in the invention can be formed using methods described in U.S. Pat. Nos. 6,136,029 and 6,296,667, the entirety of which are incorporated by reference herein. In a preferred embodiment, the reticulated bioceramic framework is formed by combining a ceramic powder with an organic binder and water to form a dispersion. The dispersion is applied to the surface of an organic reticulated foam, such as various commercially available foams made of a polyurethane, polyester, polyether, or the like. The dispersion is used to wet the surface of the foam, thereby coating the foam with the ceramic material. Wetting agents and other viscosity control agents can also be used in the ceramic dispersion as needed. Once coated, the reticulated foam is then heated to remove residual solvent. Thereafter, the coated structure is heated to sintering temperatures at which the ceramic particles at least partially sinter in order to form a rigid framework that mimics the configuration of the reticulated foam. The organic foam material pyrolyzes at or before the ceramic sintering temperature, leaving behind the ceramic framework. The pyrolyzing or oxidizing temperatures for most organics are in the range of about 200° C. to about 600° C., and the sintering temperatures for most ceramics are in the range of 1100° C. to about 1600° C.

In a preferred embodiment, the resulting bioceramic reticulated framework is essentially completely continuous and self-interconnected in three dimensions and the void volume defined within the reticulated framework is also essentially completely continuous and self-interconnected in three dimensions. Thus, these two three dimensionally interconnected parts (i.e., the void volume and the bioceramic struts) are intercollated with one another. This is sometimes referred to as 3-3 connectivity structure, wherein the first number refers to the number of dimensions in which the load-bearing framework is connected and the second number refers to the number of dimensions in which the void volume is connected.

Alternatively, in a less preferred embodiment, the bioceramic reticulated framework can be self-interconnected in three dimensions and the void volume defined within the reticulated framework can be self-interconnected in only two dimensions. This is sometimes referred to as 3-2 connectivity.

The opening sizes in the reticulated framework are preferably at least about 50 µm and more preferably about 75 µm to about 600 µm. In one embodiment, the pores have an average size of about 100 to about 400 µm. These interconnecting openings serve several purposes. First, the openings or pores in the reticulated framework should be of sufficient size to allow wicking of a liquid composition into the structure in order to facilitate integration of the calcium sulfate composition into the void volume of the reticulated framework. Additionally, the interconnected openings of the framework provide scaffolding for cellular ingrowth and vascularization during the healing process after being implanted. The porosity of the reticulated framework is preferably at least about 80% by volume, more preferably at least about 85%, most preferably at least about 90%.

Prior to incorporation of the calcium sulfate composition, the reticulated framework can be in a variety of suitable shapes and forms, such as pellets, granules, wedges, blocks and disks of various sizes. In one preferred embodiment, the reticulated framework is in the form of granules, preferably granules having an average particle size of up to 4 mm using the sieve numbering system for U.S. standard testing sieves. In one embodiment, the granules have a size of about 1 mm to about 4 mm, including granules having an average particle size of about 1 mm, about 1.8 mm, about 1.4 mm, about 1.7 mm, about 2.00 mm, about 2.36 mm, about 2.8 mm, about 3.35 mm, and about 4.00 mm.

As noted above, a solid, non-porous composition preferably substantially fills the interstitial void volume of the reticulated framework and is in intimate direct contact with the reticulated framework. The void-filling composition comprises calcium sulfate and may comprise additional ingredients as desired. The calcium sulfate used in the composition is preferably α-calcium sulfate hemihydrate, β-calcium sulfate hemihydrate, calcium sulfate dihydrate, or a mixture thereof.

The calcium sulfate composition is typically applied to the reticulated framework as an aqueous solution. The aqueous solution typically comprises sterile water and, optionally, one or more additives selected from the group consisting of inorganic salts and surface active agents such as sodium chloride, potassium chloride, sodium sulfate, potassium sulfate, EDTA, ammonium sulfate, ammonium acetate, and sodium acetate. In one preferred embodiment, the aqueous mixing solution used in the calcium phosphate composition is a saline solution or a phosphate buffered saline solution. An exemplary aqueous solution is 0.9% NaCl saline solution available from Baxter International of Deerfield, Ill.

The calcium sulfate solution can include additional ingredients. For example, the calcium sulfate composition can include an accelerant adapted for accelerating the conversion of calcium sulfate hemihydrate to calcium sulfate dihydrate. Exemplary accelerants include calcium sulfate dihydrate, potassium sulfate, and sodium sulfate. Other examples of accelerants include ionic salts. Optionally, the accelerant can be coated with sucrose.

Another example of an additive for the calcium sulfate composition is a plasticizer designed to alter the consistency and setting time of the composition. Exemplary plasticizers include glycerol and other polyols, vinyl alcohol, stearic acid, hyaluronic acid, cellulose derivatives and mixtures thereof. Alkyl celluloses are particularly preferred as the plasticizer ingredient. Exemplary alkyl celluloses include methylhydroxypropylcellulose, methylcellulose, ethylcellulose, hydroxyethylcellulose, hydroxypropylcellulose, hydroxypropylmethylcellulose, carboxymethylcellulose, cellulose acetate butyrate, and mixtures or salts thereof.

The calcium sulfate composition may further include one or more biologically active agents. As used herein, the term "biologically active agent" is directed to any agent, drug, compound, composition of matter or mixture that provides some pharmacologic affect that can be demonstrated in vivo or in vitro. Examples of biologically active agents include, but are not limited to, peptides, proteins, enzymes, small molecule drugs, dyes, lipids, nucleosides, oligonucleotides, polynucleotides, nucleic acids, cells, viruses, liposomes, microparticles, and micelles. It includes agents that produce a localized or systemic effect in a patient. Particularly preferred classes of biologically active agents include osteoinductive or osteoconductive materials, antibiotics, chemotherapeutic agents, and analgesics. Exemplary antibiotics include tetracycline hydrochloride, vancomycin, cephalosporins, and aminoglycocides such as tobramycin and gentamycin. Exemplary chemotherapeutic agents include cis-platinum, ifosfamide, methotrexate, and doxorubicin hydrochloride. Exemplary analgesics include lidocaine hydrochloride, bipivacaine and non-steroidal anti-inflammatory drugs such as ketorolac tromethamine. In one embodiment, the biologically active agent is a growth factor (natural or recombinant), such as transforming growth factors (e.g., TGF-α, TGF-β), bone morphogenic proteins (BMPs), such as any of BMP-1 to BMP-18, LIM mineralization proteins (LMPs), osteogenic proteins (e.g., OP-1, OP-2, or OP-3), demineralized bone matrix (DBM), basic fibroblast growth factor, platelet-derived growth factor, insulin-like growth factors, angiogenic factors, cytokines, interleukins, osteopontin, osteonectin, and other polypeptide growth factors.

In one preferred embodiment, the calcium sulfate composition chemically reacts to form a solid composition that substantially fills or plugs the entirety of the interstitial void volume of the reticulated framework. As used herein, the term "substantially filling" means the calcium sulfate composition fills at least about 80% of the interstitial void volume of the reticulated framework, more preferably at least about 90% of the interstitial void volume, most preferably at least about 95% of the interstitial void volume, and in certain embodiments at least about 99% of the void volume. In some preferred embodiments, approximately 100% of the void volume is filled with the calcium sulfate composition. The calcium sulfate composition that preferably fills the interstitial volume of the reticulated framework also preferably coats the outer surface of the framework.

In this preferred embodiment, the calcium sulfate void-filling composition is substantially non-porous, meaning that the calcium sulfate does not include an interconnecting pore network such that a liquid poured onto one surface of the reticulated framework will not be able to penetrate the calcium sulfate, pass through the framework, and exit the framework via a different surface.

In an alternative embodiment, the calcium sulfate composition does not substantially fill or plug the entirety of the interstitial void volume of the reticulated framework. Rather, the calcium sulfate composition fills only at least about 50% of the interstitial void volume of the reticulated framework in this embodiment. Thus, the calcium sulfate composition is deposited essentially as a thick coating on the bioceramic struts such that a liquid could be poured through the reticulated framework from one surface to another.

Once the calcium sulfate has been incorporated into the reticulated framework, the synthetic bone substitute material is preferably about 30 to about 99 percent by volume calcium sulfate, and more preferably about 50 to about 90 percent by volume calcium sulfate. The synthetic bone substitute material is preferably about 1 to about 70 percent by volume bioceramic struts (e.g., calcium triphosphate struts), more preferably about 20 to about 50 percent by volume bioceramic struts. In one embodiment, the bioceramic calcium triphosphate struts comprise about 40 percent by volume of the bone substitute material, and calcium sulfate comprises about 60 percent by volume.

To form the synthetic bone substitute material of the invention, the calcium sulfate composition can be applied to the reticulated framework using several different methods. First, an aqueous calcium sulfate composition can be injected into the pores of the reticulated framework and allowed to chemically react to form a solid composition. Alternatively, the reticulated framework can be immersed within an aqueous calcium sulfate composition such that the calcium sulfate composition is allowed to wick into the pores of the reticulated framework and thereafter set or harden into a solid.

The immersion method is particularly well-suited for a reticulated framework in the form of granules. The granules can be immersed in the calcium sulfate material and the material stirred for several minutes to promote intimate contact between the calcium sulfate solution and the pores of the granules. It typically only takes a few minutes to substantially fill the interstitial void volume of the reticulated framework with the calcium sulfate composition. Once the calcium sulfate solution is allowed to wick into the reticulated framework, the granules can be removed from the aqueous solution and allowed to dry and harden.

Alternatively, the slurry of granules can be allowed to chemically set or harden into a composition comprising a solid matrix composition formed from the calcium sulfate solution and a discontinuous phase within the calcium sulfate matrix, the discontinuous phase comprising a plurality of bioceramic reticulated framework granules having the calcium sulfate composition substantially filling the interstitial void volume thereof. FIG. 3 illustrates a cross-sectional view of an exemplary slurry 20 prepared according to this method. As shown, the slurry comprises a matrix 22 of calcium sulfate and a discontinuous phase comprising a plurality of bioceramic reticulated framework granules 24.

After this composition is allowed to harden, it is preferably granulated or cut into other shapes or sizes as desired. If granulated, the resulting granules preferably have an average particle size in the range of about 8 mm or less. In one preferred embodiment, the resulting granules have an average particle size of about 4 mm to about 8 mm as measured using U.S. standard testing sieves (e.g., granules having an average particle size of 4.00 mm, 4.75 mm, 5.6 mm, 6.3 mm, 6.7 mm, and 8.0 mm).

In one preferred embodiment, the aqueous calcium sulfate composition that is applied to the reticulated framework comprises about twelve parts by weight of calcium sulfate and about three to six parts per weight water, based on the total weight of the solution. When present, the remaining additives are typically present at a concentration of no more than about 6 parts per weight based on the initial weight of the composition.

In yet another aspect of the invention, the above-described synthetic bone substitute material is added, in granular form, to a synthetic malleable bone graft substitute composition to form a malleable composition having the consistency of a putty or paste. In this aspect of the invention, the granules are added to a composition comprising an aqueous mixing solution, calcium sulfate, a plasticizer, and, optionally, demineralized bone matrix. In one embodiment, granules of the synthetic bone substitute material of the invention are added to the commercially available ALLOMATRIX® injectable putty available from Wright Medical Technology, Inc. In this embodiment, once mixed, the bone graft substitute composition typically comprises about 5% to 50% calcium sulfate by weight, about 0.05% to 10% plasticizer by weight, about 5% to 50% by weight of the aqueous mixing solution, about 5% to about 80% by weight of the granules of the invention, and optionally, about 2% to about 50% by weight of demineralized bone matrix, based on the total weight of the composition. Exemplary aqueous solutions, calcium sulfate materials, and plasticizers suitable for use in this aspect of the invention are discussed above in connection with the calcium sulfate void-filling composition.

The demineralized bone matrix can be freeze-dried or air-dried and preferably has a moisture content of about 10 to about 30 weight percent. The demineralized bone preferably has an average particle size of about 100 to about 900 μm. Demineralized bone matrix is commercially available from Allosource (Denver, Colo.) or DCI (Nashville, Tenn.).

The malleable putty or paste composition comprising granules of the synthetic bone substitute material of the invention can be provided in the form of a kit, wherein the aqueous mixing solution and dry powder or granule components are provided in separate containers. The calcium sulfate is preferably provided in powder form and premixed with the plasticizer. Granules of bone substitute material may be premixed with the calcium sulfate and/or plasticizer powder or provided in a separate container. Optionally, the kit may further include demineralized bone matrix, either in a separate container or premixed with the calcium sulfate, granules of bone substitute material, plasticizer, or any blend thereof. The kit will also typically contain a mixing bowl, a spatula, and a set of written instructions for use. The surgeon can mix the aqueous solution with the dry ingredients (e.g., the calcium sulfate powder, plasticizer, and granules of bone substitute material, optionally blended together) and then add additional ingredients as necessary according to the invention. Once a homogeneous mixture is formed, the resulting paste or putty can be shaped into the desired form. Depending on the type of calcium sulfate contained in the putty, the shaped paste or putty may set into a hardened structure. For example, if calcium sulfate hemihydrate is used in the putty, a chemical reaction between the aqueous mixing solution and the calcium sulfate will take place, resulting in hardening of the putty over time. Alternatively, calcium sulfate dihydrate can be used as the calcium sulfate component of the putty, resulting in a putty that will maintain its malleability for an extended period of time rather than harden.

The calcium sulfate packed reticulated framework of the invention provides a bone substitute material that exhibits a dual resorption rate. The calcium sulfate will resorb more quickly than the bioceramic struts of the reticulated framework, thereby allowing ingress of vasculature and bone ingrowth. The calcium sulfate also provides additional structural support and strength that improves stability of the reticulated structure and reduces the risk of damaging the framework during handling.

In yet another aspect of the invention, a method for treating a bone defect is provided, wherein the synthetic bone substitute material of the invention is applied to the site of a bone defect in a patient. The term "patient" encompasses any animal with an endoskeleton frame, particularly mammals (e.g., humans, dogs, cats, horses, and the like). The synthetic bone substitute material may be applied to the site of the bone defect in any of the variety of forms discussed above. For example, the synthetic bone substitute material can be applied to the surgical site in the form of pellets, granules, wedges, blocks and disks. The synthetic bone substitute material can also be applied in the form of a hardened and shaped bone graft substitute material formed using the synthetic malleable bone graft substitute composition described above.

The synthetic bone substitute material described above can be used by itself as a bone graft material, whether in granule, wedge, block, disk, or other standardized form. If desired, the synthetic bone substitute material can be used in a non-standard shape based on the precise dimensions of the bone void or defect that is to be repaired. In one preferred embodiment, the synthetic bone substitute material is used as a bone graft composition in granular form, wherein the granules are applied as a packing at the anatomical site where the bone defect is located. The granules are used to substantially fill the dimensions of the bone void or defect. In another embodiment, the synthetic bone substitute material of the invention is mixed with autologous bone marrow aspirate and applied to the bone defect in the form of a clotted mass of defined shape.

EXPERIMENTAL $CaSO_4$ Filled Tricalcium Phosphate (TCP) Granules

Materials:
4.5 g (~10 cc) 1-4 mm CELLPLEX® TCP porous granules
12 g $CaSO_4$ hemihydrate
4 g Sterile water
Mixing Bowl
Spatula Mixing Method:
1. In the mixing bowl, combine the CaSO4 hemihydrate and sterile water.
2. Stir the $CaSO_4$ and water mixture until a flowable homogeneous paste has been created.
3. Add the CELLPLEX® TCP granules to the $CaSO_4$ mixture.
4. Gently fold the CELLPLEX® TCP granules into the $CaSO_4$ mixture until the $CaSO_4$ has fully impregnated the porous structure.
5. Remove the $CaSO_4$ filled TCP mixture from the bowl and separate or mold into the desired size or shape.
6. Allow separated shapes to air dry until firm.
7. If further granulation is desired, granulate the dried material as appropriate.
8. If desired, oven dry the mixture to remove non-covalently bound moisture.

Many modifications and other embodiments of the inventions set forth herein will come to mind to one skilled in the art to which these inventions pertain having the benefit of the teachings presented in the foregoing descriptions and the associated drawing. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A synthetic bone substitute material suitable for use as a replacement for cancellous bone in a bone graft composition comprising a reticulated framework comprising a plurality of interconnecting bioceramic struts and defining an interconnecting interstitial void volume; and a solid, non-porous composition within said interstitial void volume and in intimate contact with said reticulated framework, wherein said solid, non-porous composition comprises calcium sulfate, which does not include an interconnecting pore network such that a liquid poured onto one surface of the reticulated framework can not penetrate the calcium sulfate, pass through the framework, and exit the framework via a different surface.

2. The synthetic bone substitute material of claim 1, wherein said solid, non-porous composition coats an outer surface of said reticulated framework.

3. The synthetic bone substitute material of claim 1, wherein the bone substitute material is in a form selected from the group consisting of pellets, granules, wedges, blocks, and disks.

4. A synthetic bone substitute material suitable for use as a replacement for cancellous bone in a bone graft composition comprising a solid matrix composition comprising calcium sulfate; and a discontinuous phase within said matrix, said discontinuous phase comprising a plurality of granules, each granule comprising a reticulated framework comprising a plurality of interconnecting bioceramic struts and defining an interconnecting interstitial void volume; and a solid, non-porous composition within said interstitial void volume and in intimate contact with said reticulated framework, wherein said solid, non-porous composition comprises calcium sulfate, which does not include an interconnecting pore network such that a liquid poured onto one surface of the reticulated framework can not penetrate the calcium sulfate, pass through the framework, and exit the framework via a different surface.

5. The synthetic bone substitute material of claim 4, wherein the bone substitute material is in granulated form.

6. The synthetic bone substitute material of claim 5, wherein the bone substitute material is in the form of granules having an average particle size of less than about 8 mm.

7. The synthetic bone substitute material of claim 1, wherein the reticulated framework defines interstitial openings having a size of about 50 to about 600 μm.

8. The synthetic bone substitute material of claim 1, wherein the bioceramic struts are formed of a ceramic material selected from the group consisting of alumina, zirconia, calcium phosphate, silica based glass, pyrolytic carbon, and combinations thereof.

9. The synthetic bone substitute material of claim 8, wherein the bioceramic struts are formed of sintered calcium phosphate.

10. The synthetic bone substitute material of claim 9, wherein the calcium phosphate is selected from the group consisting of hydroxyapatite, tricalcium phosphate, tetracalcium phosphate, anhydrous dicalcium phosphate, monocalcium phosphate monohydrate, dicalcium phosphate dihydrate, heptacalcium phosphate, octocalcium phosphate, calcium pyrophosphate, oxyapatite, calcium metaphosphate, carbonatoapatite, dahlite, and combinations thereof.

11. The synthetic bone substitute material of claim 9, wherein the calcium phosphate is selected from the group consisting of α-tricalcium phosphate, β-tricalcium phosphate, and combinations thereof.

12. The synthetic bone substitute material of claim 1, wherein the calcium sulfate is selected from the group consisting of α-calcium sulfate hemihydrate, β-calcium sulfate hemihydrate, calcium sulfate dihydrate, and mixtures thereof.

13. The synthetic bone substitute material of claim 1, wherein the solid, non-porous composition further comprises demineralized bone matrix.

14. The synthetic bone substitute material of claim 1, wherein the solid, non-porous composition further comprises an accelerant.

15. The synthetic bone substitute material of claim 14, wherein the accelerant is calcium sulfate dihydrate, sucrose-coated calcium sulfate dihydrate, alkali metal sulfates, and mixtures thereof.

16. The synthetic bone substitute material of claim 1, wherein the solid, non-porous composition further comprises a plasticizer.

17. The synthetic bone substitute material of claim 16, wherein the plasticizer is selected from the group consisting of glycerol, vinyl alcohol, stearic acid, hyaluronic acid, cellulose derivatives, and mixtures thereof.

18. The synthetic bone substitute material of claim 16, wherein the plasticizer is a cellulose derivative selected from the group consisting of methylhydroxypropylcellulose, methylcellulose, ethylcellulose, hydroxyethylcellulose, hydroxypropylcellulose, hydroxypropylmethylcellulose, carboxymethylcellulose, cellulose acetate butyrate, and mixtures or salts thereof.

19. The synthetic bone substitute material of claim 1, wherein the solid, non-porous composition further comprises a biologically active agent.

20. The synthetic bone substitute material of claim 19, wherein the biologically active agent is selected from the group consisting of growth factors, antibiotics, chemotherapeutic agents, and analgesics.

21. The synthetic bone substitute material of claim 1, comprising about 30 to about 99 percent calcium sulfate by volume and about 1 to about 70 percent bioceramic struts by volume.

22. The synthetic bone substitute material of claim 4, comprising about 30 to about 99 percent calcium sulfate by volume and about 1 to about 70 percent bioceramic struts by volume.

23. A synthetic bone substitute material suitable for use as a replacement for cancellous bone in a bone graft composition comprising a plurality of granules, each granule comprising about 1 to about 70 percent by volume of a reticulated framework comprising a plurality of interconnecting calcium phosphate struts and defining an interconnecting interstitial void volume; and about 30 to about 99 percent by volume of a solid, non-porous composition within said interstitial void volume and in intimate contact with said reticulated framework, wherein said solid, non-porous composition comprises calcium sulfate, which does not include an interconnecting pore network such that a liquid poured onto one surface of the reticulated framework can not penetrate the calcium sulfate, pass through the framework, and exit the framework via a different surface.

* * * * *